United States Patent
Ogo

(10) Patent No.: US 11,124,820 B2
(45) Date of Patent: Sep. 21, 2021

(54) SAMPLE PROCESSING METHOD AND SAMPLE CULTURING METHOD

(71) Applicant: OLYMPUS CORPORATION, Hachioji (JP)

(72) Inventor: Katsunori Ogo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 253 days.

(21) Appl. No.: 16/222,862

(22) Filed: Dec. 17, 2018

(65) Prior Publication Data

US 2019/0185901 A1    Jun. 20, 2019

(30) Foreign Application Priority Data

Dec. 20, 2017  (JP) .............................. JP2017-243365

(51) Int. Cl.
| | |
|---|---|
| *C12Q 1/02* | (2006.01) |
| *C12M 1/00* | (2006.01) |
| *C12M 1/22* | (2006.01) |
| *C12M 1/34* | (2006.01) |
| *C12M 1/12* | (2006.01) |
| *B01J 2/08* | (2006.01) |

(52) U.S. Cl.
CPC .................. *C12Q 1/02* (2013.01); *B01J 2/08* (2013.01); *C12M 23/10* (2013.01); *C12M 25/01* (2013.01); *C12M 29/06* (2013.01); *C12M 41/36* (2013.01); *C12Y 402/99* (2013.01); *C12N 2533/74* (2013.01); *Y10S 423/14* (2013.01)

(58) Field of Classification Search
CPC . C12Q 1/02; B01J 2/08; C12Y 402/99; Y10S 423/14; C12N 2533/74
See application file for complete search history.

(56) References Cited

U.S. PATENT DOCUMENTS

| | | |
|---|---|---|
| 2005/0014254 A1 | 1/2005 | Kruse |
| 2006/0293169 A1 | 12/2006 | Srinivasan et al. |
| 2007/0037281 A1 | 2/2007 | Kruse |
| 2010/0210771 A1 | 8/2010 | Leyrer et al. |
| 2010/0252118 A1 | 10/2010 | Fraden et al. |

(Continued)

FOREIGN PATENT DOCUMENTS

| | | |
|---|---|---|
| DE | 10362002 B4 | 10/2006 |
| GB | 2539935 A | 1/2017 |

(Continued)

OTHER PUBLICATIONS

Ahn, et al., "Fabrication of cell-laden three dimensional alginate-scaffolds with an aerosol cross-linking process", Journal of Materials Chemistry, Jan. 1, 2012, vol. 22, No. 36, p. 18735.

(Continued)

*Primary Examiner* — Taeyoon Kim
(74) *Attorney, Agent, or Firm* — Holtz, Holtz & Volek PC

(57) ABSTRACT

Provided is a sample processing method that liquefies a medium solution by making a liquid that liquefies the medium solution act on a sample formed by gelating or solidifying the medium solution that is supported by a substrate while an observation subject is included therein, while maintaining a state in which the medium solution is supported by the substrate while the observation subject is included therein.

12 Claims, 8 Drawing Sheets

(56) References Cited

U.S. PATENT DOCUMENTS

| | | | |
|---|---|---|---|
| 2011/0306110 A1 | 12/2011 | Takeuchi et al. | |
| 2011/0306122 A1 | 12/2011 | Moritz et al. | |
| 2014/0212965 A1 | 7/2014 | Kruse | |
| 2016/0201050 A1* | 7/2016 | Zimmermann | B01J 13/206 435/178 |
| 2016/0220997 A1 | 8/2016 | Mescher et al. | |
| 2016/0369218 A1 | 12/2016 | Kamei et al. | |
| 2017/0341941 A1 | 11/2017 | Zhao et al. | |
| 2018/0216046 A1 | 8/2018 | Agerkhed et al. | |

FOREIGN PATENT DOCUMENTS

| | | |
|---|---|---|
| JP | H10248557 A | 9/1998 |
| JP | 5177774 B2 | 4/2013 |
| JP | 5490803 B2 | 5/2014 |
| WO | 2015129673 A1 | 9/2015 |
| WO | 2017001680 A1 | 1/2017 |

OTHER PUBLICATIONS

Comley, "Progress made in applying 3D cell culture technologies", Drug Discovery World, Jan. 1, 2013, pp. 41-58.

Leong, et al., "In Vitro Growth of Human Keratinocytes and Oral Cancer Cells into Microtissues: An Aerosol-Based Microencapsulation Technique", Bioengineering, May 14, 2017, vol. 4, No. 4, p. 43.

Ikki Horiguchi, et al., "Proliferation and pluripotency of iPS cells in alginate hydrogel-based microcapsules," Seisan Kenkyu, vol. 64, Issue 3, pp. 341-344, DOI: https://doi.org/10.11188/seisankenkyu.64.341.

Mark Mercola, et al., "Induced Pluripotent Stern Cells in Cardiovascular Drug Discovery," Circulation Research, 2013, 112, pp. 523-533, URL: https://www.ahajournals.org/doi/pdf/10.1161/CIRCRESAHA.111.250266.

Masahiro Kawai, et al., "The Effect of Added Salt on Gelation by Divalent Metal Ions of Alginate Aqueous Solution," Journal of the Chemical Society of Japan, 1993(10), pp. 1184-1187.

Therese Andersen, et al., "3D Cell Culture in Alginate Hydrogels," Microarrays 2015, 4(2), pp. 133-161.

U.S. Appl. No. 16/176,976, First Named Inventor: Katsunori Ogo, Title: "Method for Preparing Sample for Microscope Examination and Sample Preparation Kit," filed Oct. 31, 2018.

Waseem Asghar, et al., "In Vitro Three-Dimensional Cancer Culture Models," URL: https://www.researchgate.net/publication/282769044_In_Vitro_Three-Dimensional_Cancer_Culture_Models.

U.S. Appl. No. 16/222,739, First Named Inventor: Katsunori Ogo, Title: "Microscope-Observation-Sample Preparation Base Material and Microscope-Observation-Sample Preparation Method," filed Dec. 17, 2018.

How to Unclog your Foam Pump Bottle, thediysecrets, 2014, accessed at <http://www.thediysecrets.com/ how-to-unclog-your-foam-pump-bottle/> (Year: 2014).

Office Action (Non-Final Rejection) dated Mar. 19, 2021 issued in related U.S. Appl. No. 16/222,739.

* cited by examiner

BRIGHT-FIELD

FLUORESCENCE

SAMPLE PROCESSING METHOD AND SAMPLE CULTURING METHOD

CROSS-REFERENCE TO RELATED APPLICATIONS

This application is based on Japanese Patent Application No. 2017-243365, the content of which is incorporated herein by reference.

TECHNICAL FIELD

The present invention relates to a sample processing method and a sample culturing method.

BACKGROUND ART

In recent years, microscope observation of a three-dimensionally cultured cell aggregates, such as spheroids or organoids, has attracted attention. In terms of production of a cell aggregate, there is a known method in which, for example, cells, together with a culturing liquid, are dispensed onto an inner surface of a lid of a petri dish in the form of a droplet, a hanging drop is formed by inverting the droplet, and cells are aggregated inside the hanging drop in a direction along the curved surface of the hanging drop assisted by a component of gravity (for example, see Patent Literature 1).

There is a known multiwell-plate structure that improves the technology of Patent Literature 1 and that is capable of forming hanging drops suitable for automation of cell-aggregate production (for example, see Patent Literature 2). The multiwell plate described in Patent Literature 2 is configured by arranging, in an array-like manner, sets of depressions that receive a liquid discharged from a dispenser, hanging-drop-forming sections in which hanging drops are formed and stored, and ducts enabling communication between these components. The multiwell plate described in Patent Literature 2 does not require inversion of the droplets as in the method described in Patent Literature 1, and is capable of forming the hanging drops just by dispensing cells, a culturing liquid, and the like from above the multiwell plate in accordance with the array arrangement format, thus facilitating automation of cell-aggregate production in the hanging drops.

There is a known technology that is developed from the technology of Patent Literature 2 and that enables detailed observation and image acquisition by means of a microscope (for example, see Patent Literature 3). With the technology described in Patent Literature 3, produced cell aggregates in hanging drops are dropped, together with the hanging drops, onto wells of a multiwell plate having transparent flat bottom surfaces, and observation and image acquisition are performed by collecting, via the bottom surfaces of the wells, light emitted from the cell aggregates by using an objective lens of an inverted microscope.

There is a known technology that has been further developed from the technology of Patent Literature 3, and that is capable of immobilizing cell aggregates so as not to come into contact with bottom surfaces of wells (for example, see Patent Literature 4). With the technology described in Patent Literature 4, a cell/alginic-acid mixture is dripped into a calcium chloride solution in a centrifuge tube, thereby forming beads in the solution as a result of alginic acid gelating in the centrifuge tube, and thus, a sample that includes cultured cells in bead-like alginic-acid gel is formed. In addition, with the technology described in Patent Literature 4, the bead-like alginic-acid gel is immersed in an aqueous solution of a chelating agent and is dissolved in an aqueous solution, thus recovering and re-culturing the cultured cells.

CITATION LIST

Patent Literature

{PTL 1} Publication of German Patent No. 10362002, Specification
{PTL 2} Publication of Japanese Patent No. 5490803
{PTL 3} PCT International Publication No. WO 2017/001680
{PTL 4} Japanese Unexamined Patent Application, Publication No. Hei 10-248557

SUMMARY OF INVENTION

A first aspect of the present invention is a sample processing method including liquefying a medium solution by making a liquid that liquefies the medium solution act on a sample formed by gelating or solidifying the medium solution that is supported by a substrate while an observation subject is included therein, while maintaining the state in which the medium solution is supported by the substrate while the observation subject is included therein.

With this aspect, the state in which the medium solution is supported by the substrate while the observation subject is included therein is maintained even after the medium solution is liquefied. By doing so, it is possible to perform work such as medium exchange, continuous culturing, and the like on the same substrate. In addition, it is possible to prevent the observation subject from being exposed to the liquid, which liquefies the medium solution, as a result of the observation subject becoming exposed, and it is also possible to prevent the observation subject from adhering to a bottom surface of the container accommodating the liquid or changing the form thereof as a result of coming into contact with the bottom surface of the container. Therefore, with the sample formed by gelating or solidifying the medium solution in which the observation subject is included, it is possible to perform recovery of the observation subject, medium exchange, and continuous culturing.

In the above-described aspect, the liquid may be brought into contact with a surface of the medium solution in the form of a mist, a foam, or a droplet having a smaller volume than the medium solution.

By employing such a configuration, it is possible to prevent the medium solution from being mixed and dispersed in the liquid. In addition, since only simple work of bringing the liquid into contact with the surface of the medium solution in which the observation subject is included is required, it is possible to automate the processing for liquefying the medium solution of the sample.

In the above-described aspect, the liquid may be nebulized by means of ultrasonic-wave irradiation or pressurization.

By employing such a configuration, it is possible to make the liquid into a mist in a simple manner by means of a general method.

In the above-described aspect, the liquid may be added or applied to the medium solution or the medium solution is immersed in the liquid.

By employing such a configuration, in the case in which the liquid is added to the medium solution, it is possible to add a drug or a culturing liquid by liquefying the interior of the sample while leaving the surface of the sample in a gel-like or solid state. In addition, in the case in which the medium solution is immersed in the liquid, it suffices to just store the liquid in a container, and thus, it is possible to simplify the apparatus.

In the above-described aspect, the liquid may liquefy the medium solution by means of an oxidative decomposition reaction that decomposes cross-links in the sample in which two or more molecules are joined by cross-linking agents, a chelating reaction that eliminates joining of molecules by removing divalent cations from the sample in which two or more molecules are joined by divalent cations, or a reaction that enzymatically or chemically decomposes peptides, fibers, sugars, or lipids that impart viscoelasticity.

In the above-described aspect the liquid may be a chelating agent.

By employing such a configuration, it is possible to easily dissolve the gel-like or solid medium solution by means of the chelating agent.

In this case, the chelating agent may be formed of at least one of EDTA (ethylenediaminetetraacetic acid), EGTA (glycol ether diamine tetraacetic acid), and BAPTA 1,2-Bis(2-aminophenoxy)ethane-N,N,N',N'-tetraacetic acid).

In the above-described aspect, the liquid may contain an enzyme that exhibits alginate lyase activity.

In the above-described aspect, the substrate may have a rod-like, cup-like, well-like, ring-like, or swab-like form, a plate-like form having a flat or irregular surface, a sponge-like form, or a porous form.

In the above-described aspect, the substrate may support the medium solution including the observation subject therein in a state in which the medium solution is attached on a surface of the substrate in a droplet-like manner.

By employing such a configuration, by employing the substrate having a simple shape, it is possible to maintain the medium solution by utilizing surface tension.

In the above-described aspect, the substrate may support, in a suspended state, a droplet of the medium solution including the observation subject therein.

By employing such a configuration, it is possible to stabilize, by means of gravity, the position of the observation subject in the droplet of the medium solution while maintaining a state in which the droplet is separated from a well or the like.

In the above-described aspect, the sample may possess viscoelasticity due to alginic-acid hydrogel.

In the above-described aspect, the observation subject may be a biological origin material formed of cells, cell aggregates, cellular tissue, spheroids or organoids, or the observation subject may be a non-biological origin material that generates fluorescence, light, or phosphorescence or that has a pigment.

A second aspect of the present invention is a sample culturing method including: a step of gelating or solidifying a medium solution, which is substantially transparent when gelated or solidified, in a state in which the medium solution is supported by a substrate and includes an observation subject therein; a step of observing the observation subject that is included in the gel-like or solid medium solution supported by the substrate; and a step of, after performing observation, liquefying the medium solution by making a liquid that liquefies the medium solution act on the medium solution while maintaining the state in which the medium solution is supported by the substrate while the observation subject is included therein.

With this aspect, by gelating or solidifying the medium solution in the state in which the medium solution is supported by the substrate and the observation subject is included therein, it is possible to grow the observation subject or to change the medium in the gel-like medium solution supported by the substrate. Also, by observing the observation subject in this state, it is possible to perform highly detailed observation in which influence of the refractive index of the medium solution or the like is suppressed as compared with the case in which the medium solution is in a liquid state.

Furthermore, by liquefying the medium solution while maintaining the state in which the medium solution is supported by the substrate while the observation subject is included therein after performing observation, it is possible to perform work such as medium exchange, continuous culturing, and the like on the same substrate. In addition, it is possible to prevent the observation subject from being exposed to the liquid, which liquefies the medium solution, as a result of the observation subject becoming exposed, and it is also possible to prevent the observation subject from adhering to the bottom surface of the container accommodating the liquid or changing the form thereof as a result of coming into contact with the bottom surface of the container.

Advantageous Effects of Invention

A sample processing method and a sample culturing method according to the present invention afford an advantage in that, with a sample formed by gelating or solidifying a medium solution including cells, it is possible to easily perform cell recovery, medium exchange, and continuous culturing.

DESCRIPTION OF EMBODIMENT

A sample processing method and a sample culturing method according to an embodiment of the present invention will be described below with reference to the drawings.

Figure 1:
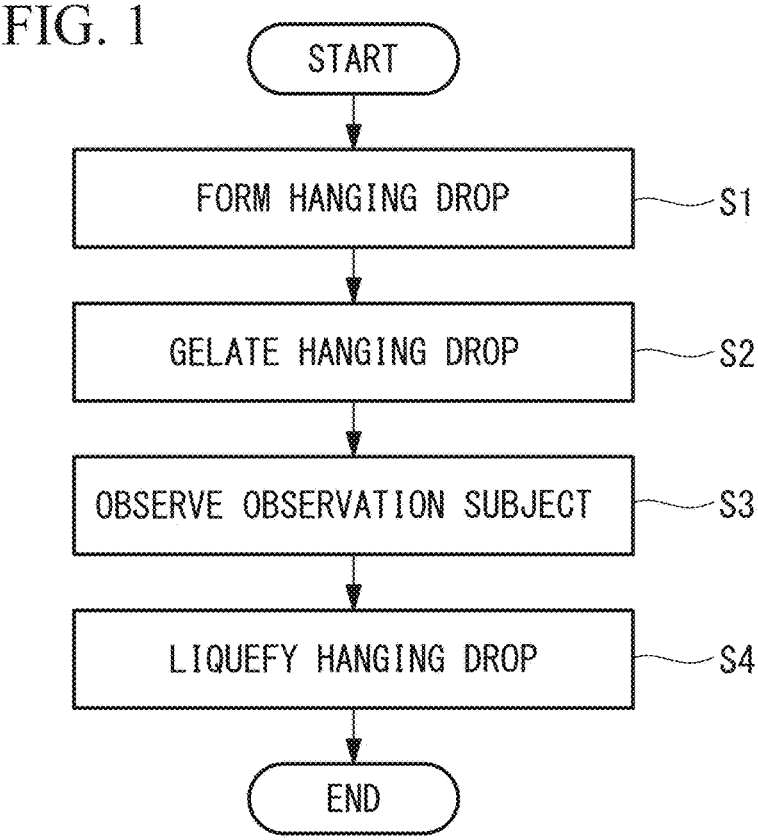
FIG. 1 is a flowchart for explaining a sample culturing method according to an embodiment of the present invention.
Figure 2:
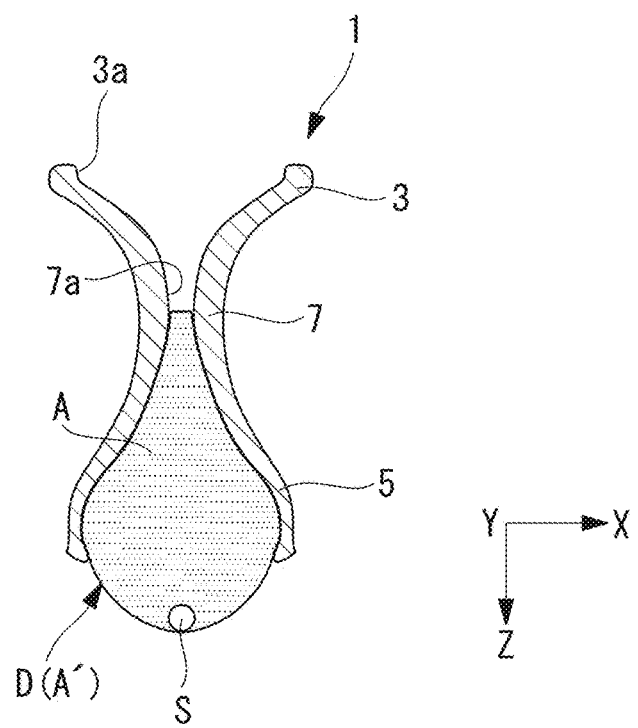
FIG. 2 is a longitudinal cross-sectional view of a hanging-drop forming device employed in the sample culturing method in FIG. 1.

As shown in the flowchart in FIG. 1, as well as FIG. 2, the sample culturing method according to this embodiment includes: a step S1 of forming a hanging drop D, in which an observation subject (biological origin material) S is included in a droplet A' of a medium solution A, by means of a hanging-drop forming device 1 in a suspended state; a step S2 of gelating the liquid hanging drop D; a step S3 of observing the observation subject S included in the gelated hanging drop D; and a step (sample processing method) S4 of, after performing observation, liquefying the hanging drop D while maintaining the state in which the hanging drop D is supported by the hanging-drop forming device 1 while the observation subject S is included therein.

As shown in FIG. 2, the hanging-drop forming device 1 is provided with, for example: a depression 3 into which the medium solution A is injected; a hanging-drop-forming section 5 that supports the droplet A' of the medium solution A injected into the depression 3 in a suspended state while the observation subject S is included in the droplet A'; and a fine duct 7 that connects the depression 3 and the hanging-drop-forming section 5.

The depression 3 has an opening 3a that is provided on the opposite side from the duct 7, and has a substantially conical shape in which the size thereof decreases in a tapered manner from the opening 3a to the duct 7.

The hanging-drop-forming section 5 has a substantially conical shape that gradually expands radially outward from the duct 7. The hanging-drop-forming section 5 supports the droplet A' of the medium solution A in such a way that a surface of a bottom portion of the droplet A' is exposed.

The duct 7 has a through-hole 7a that passes through from the depression 3 to the hanging-drop-forming section 5.

The hanging-drop forming device 1 is used in an orientation in which the depression 3 is set vertically above and the hanging-drop-forming section 5 is set vertically below. In the following, the vertical direction is assumed to be a Z-direction and two directions that are orthogonal to the Z-direction and that are orthogonal to each other are assumed to be an X-direction and a Y-direction.

In the step S2 in which the liquid hanging drop D is gelated, the droplet A' is subjected to the action of a liquid B that gelates the liquid medium solution A by means of a chemical reaction.

In the step S4 in which the gelated hanging drop D is liquefied, the droplet A' is subjected to the action of a liquid C that liquefies the gel-like medium solution A by means of a chemical reaction.

Figure 3:
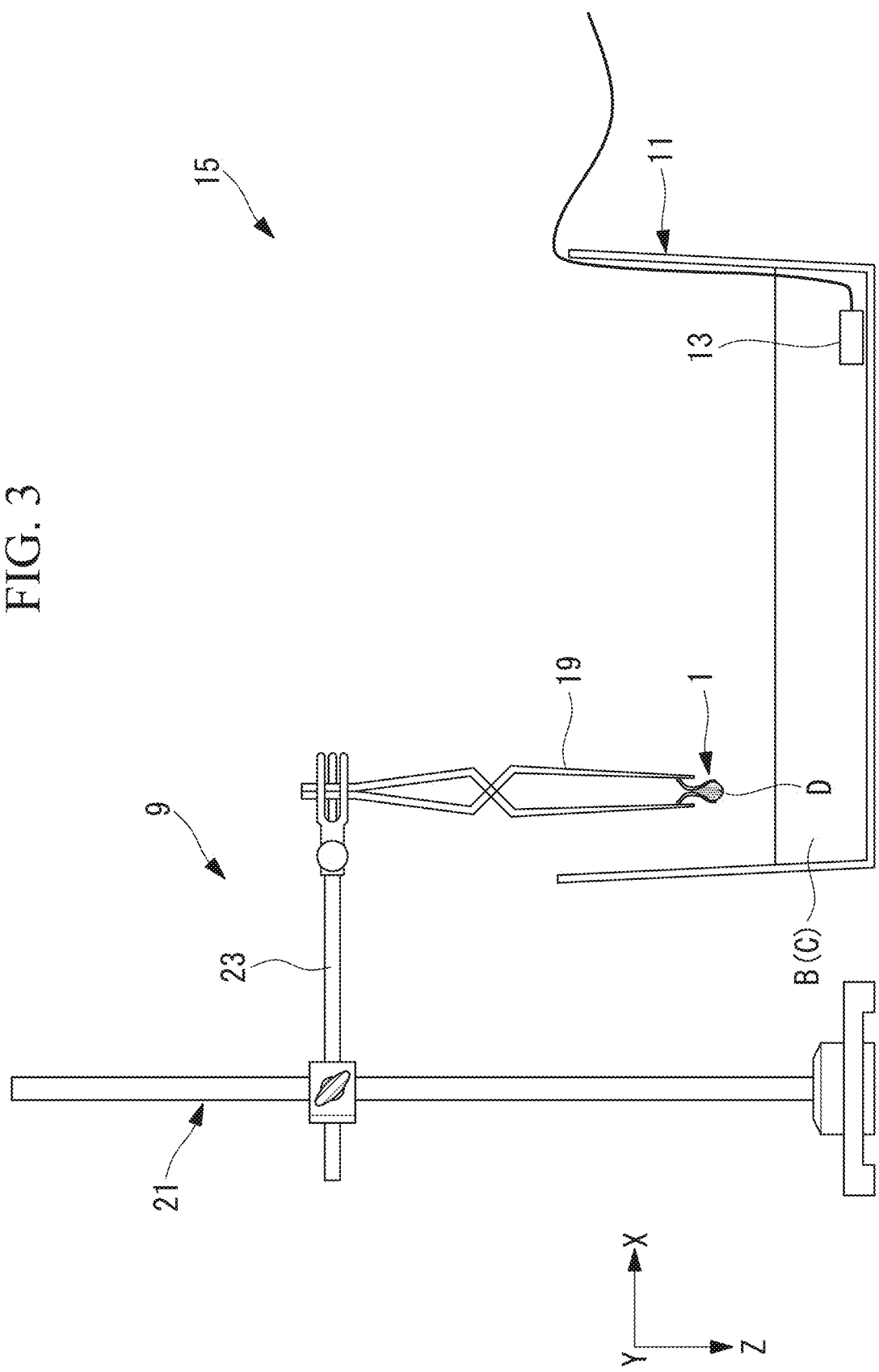
FIG. 3 is a side view showing an example of a sample processing apparatus employed in the sample culturing method in FIG. 1.

As shown in FIG. 3, the step S2 of gelating the hanging drop D and the step S4 of liquefying the gelated hanging drop D are performed by using, for example, a sample processing apparatus 15 provided with: a support 9 that supports the hanging-drop forming device 1; a container 11 that stores the liquid B or the liquid C; and an ultrasonic nebulizing apparatus 13 that makes the liquid B or the liquid C act on the hanging drop D.

The support 9 is provided with: an equipment gripper 19 that grips the hanging-drop forming device 1; a stand 21 that extends in the vertical direction; and a clamp 23 that extends from the stand 21 in a direction that intersects the vertical direction and that grips the equipment gripper 19.

The ultrasonic nebulizing apparatus 13 is disposed in the liquid B or the liquid C in the container 11, and generates ultrasonic waves to form a fine mist of the liquid B or the liquid C, thus being capable of filling the interior of the container 11 with the generated mist-like liquid B or liquid C.

As the medium solution A, for example, a sodium-alginate-containing medium that allows growth of a biological origin material is employed. The medium solution A is transparent when gelated. As long as the medium solution A contains alginate, there is no limitation with regard to the sodium salt used. In addition, although it is preferable that, in terms of weight percentage, 0.5% or a greater amount of the sodium alginate be contained, there is no limitation thereto. The specific gravity of the medium solution A is 1, which is lower than the specific gravities of cells or a spheroid.

As the liquid B, for example, a calcium-chloride aqueous solution or the like, which is an aqueous solution containing ions of a divalent metal (calcium, magnesium, strontium, or the like) is employed. Although it is preferable that the molar concentration of calcium chloride be 100 mM or greater, there is no limitation thereto.

With regard to the liquid C, in the case in which the gelated droplet A' is alginic-acid hydrogel that is generated by subjecting the sodium-alginate-containing medium solution A to the action of the liquid B containing divalent-metal ions, a chelating agent that contains a substance that bonds to the divalent-metal ions and forms a complex (performs chelation) is employed. It is possible to liquefy the gel-like droplet A' by removing, from the gel-like droplet A in which two or more molecules are joined by the divalent cations in the liquid B, the divalent cations by means of the chelating agent, thus eliminating joining of the molecules (chelating reaction). The chelating agent may be, for example, a solution containing a least one of EDTA, EGTA, and BAPTA. In addition, in addition to a chelating agent, the liquid C may be an enzyme that possesses alginate lyase activity, such as an alginic-acid decomposing enzyme or the like.

The operations of the thus-configured sample processing method and sample culturing method will be described below.

The sample processing method and the sample culturing method according to this embodiment are utilized in experimental strategies of, for example, undifferentiated-cell culturing, differentiation culturing, microscope observation and screening (classification), terminal culturing, and transplanting.

Figure 4:
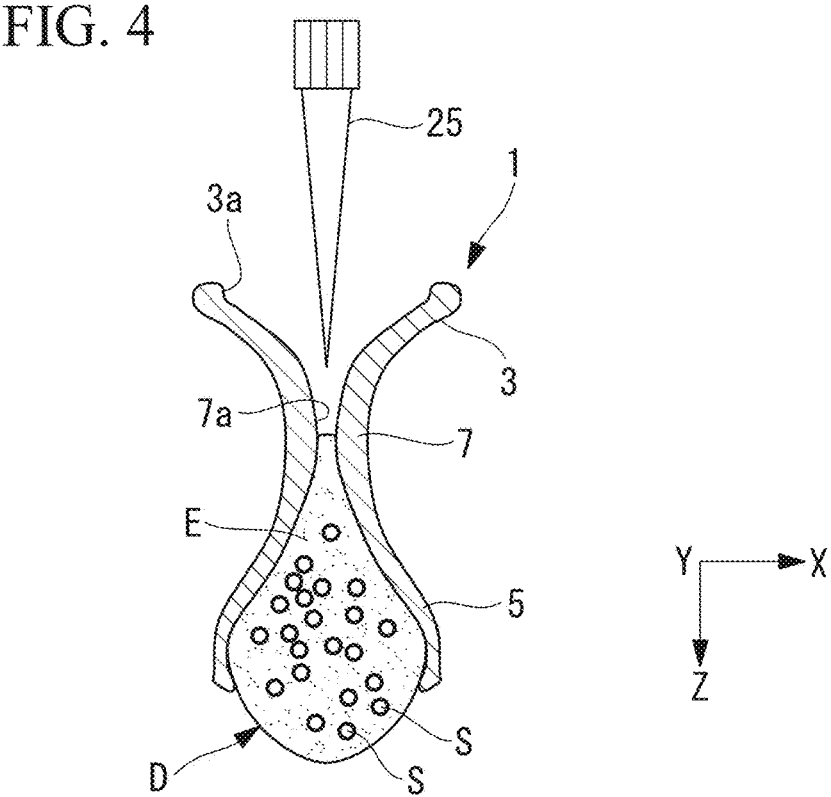
FIG. 4 is a longitudinal cross-sectional view showing an example of a liquid hanging drop formed by the hanging-drop forming device in FIG. 2.

First, as shown in FIG. 4, a plurality of cells, which serve as the observation subjects S, are dispensed together with a medium E from above the depression 3 of the hanging-drop forming device 1 by using a pipette 25. The medium E dispensed into the depression 3 moves, together with the observation subjects S, downward due to gravity through the through-hole 7a of the duct 7, and the droplet A' thereof is supported by the hanging-drop-forming section 5 in a suspended state. By doing so, the hanging drop D in which the droplet A' of the medium solution A is in a suspended state while the observation subjects S are included therein is formed (step S1).

Since the medium solution A forming the hanging drop D has a lower specific gravity than that of cells or a spheroid, observation subjects S are moved by gravity along the interface of the hanging drop D, thus settling in the vicinity of the bottommost point of the hanging drop D. Therefore, by determining the amount of the medium solution A to be dispensed into the depression 3 in advance, it is possible to maintain the positions of the observation subjects S in the hanging drops D constant not only in the X, Y-directions but also in the Z-direction. In addition, by using the hanging-drop forming device 1, there is no need to invert the droplet A' of the medium solution A in order to form the hanging drop D.

Next, the medium exchange is performed via the depression 3 from above the hanging-drop forming device 1 by using the pipette 25, thus forming a spheroid in which the plurality of cells, which serve as the observation subjects S, are aggregated (undifferentiated-cell culturing). By forming the spheroid by culturing the cells in the hanging drop D, there is no need to transfer the spheroid, which serves as the observation subject S, and thus, it is possible to increase the throughput.

Next, the medium E is exchanged via the depression 3 with the medium solution A, which serves as a differentiation medium containing sodium alginate, from above the hanging-drop forming device 1 by using the pipette 25. Then, by using the sample processing apparatus 15 shown in FIG. 3, the liquid B is made to act on the liquid hanging drop D supported by the hanging-drop forming device 1, thus gelating the hanging drop D.

Specifically, as shown in FIG. 3, the liquid B is stored in the container 11, and the hanging-drop forming device 1 in which the hanging drop D is formed is supported by the support 9 and disposed above the liquid B in the container 11. Then, the ultrasonic nebulizing apparatus 13 is activated to nebulize the liquid B, the container 11 is filled with the mist-like liquid B, and thus, the liquid B is brought into contact with a surface of the hanging drop D in a mist-like manner.

Then, the hanging drop D in this state is left standing still in the mist-like liquid B for 30 minutes, the liquid B permeates into the interior of the hanging drop D from the exposed surface thereof, and thus, the hanging drop D is gelated up to the vicinity of the area surrounding the observation subject S (step S2). By doing so, a sample in which the observation subject S in the substantially transparent hanging drop D is immobilized at a position in a bottommost portion thereof is produced. Note that only the surface of the hanging drop D may be gelated, as needed.

Figure 5:
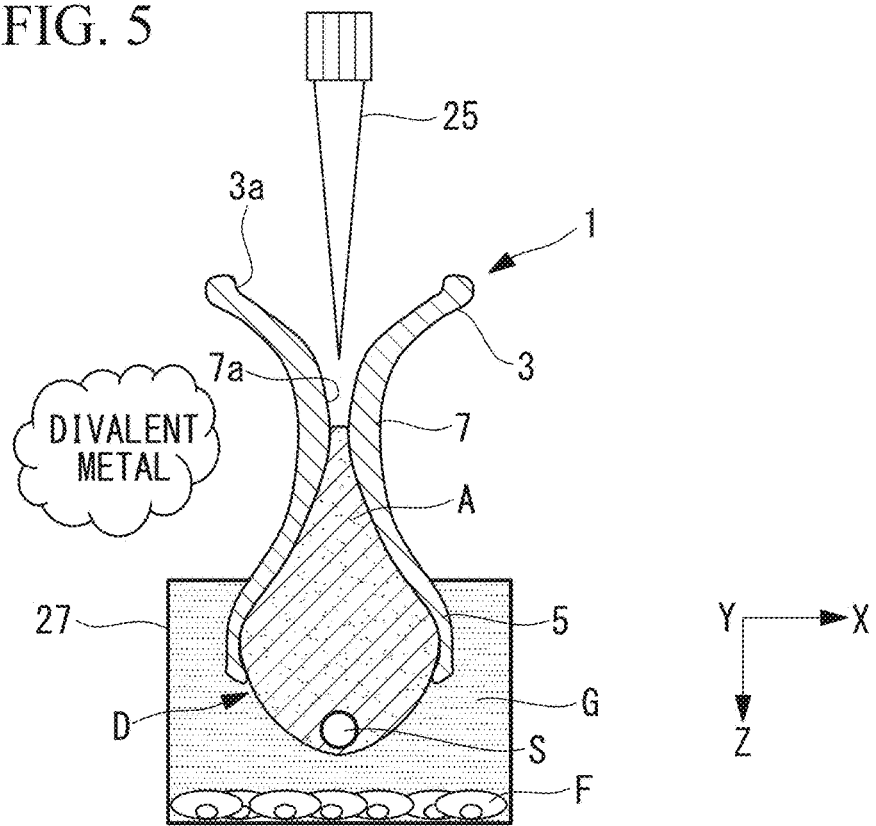
FIG. 5 is a longitudinal cross-sectional view showing a state in which the liquid hanging drop in FIG. 4 is converted into a gel-like state by being brought into contact with a liquid in a mist-like state that gelates the drop, thus performing differentiation culturing.

Next, as shown in FIG. 5, a container 27 in which feeder cells F for preparing an environment required for proliferation or differentiation of the observation subject S are spread out and a medium G is stored is prepared, and the gel-like hanging drop D supported by the hanging-drop forming device 1 is immersed in the medium G in the container 27, thus exchanging the media by means of natural diffusion (differentiation culturing).

Since the observation subject S is included in the hanging drop D, it is possible to separately culture the observation subject S and the feeder cells F, and, in addition, since the hanging drop D has been gelated, it is possible to prevent the medium solution A forming the hanging drop D from being mixed and dispersed in the medium G.

Figure 6:
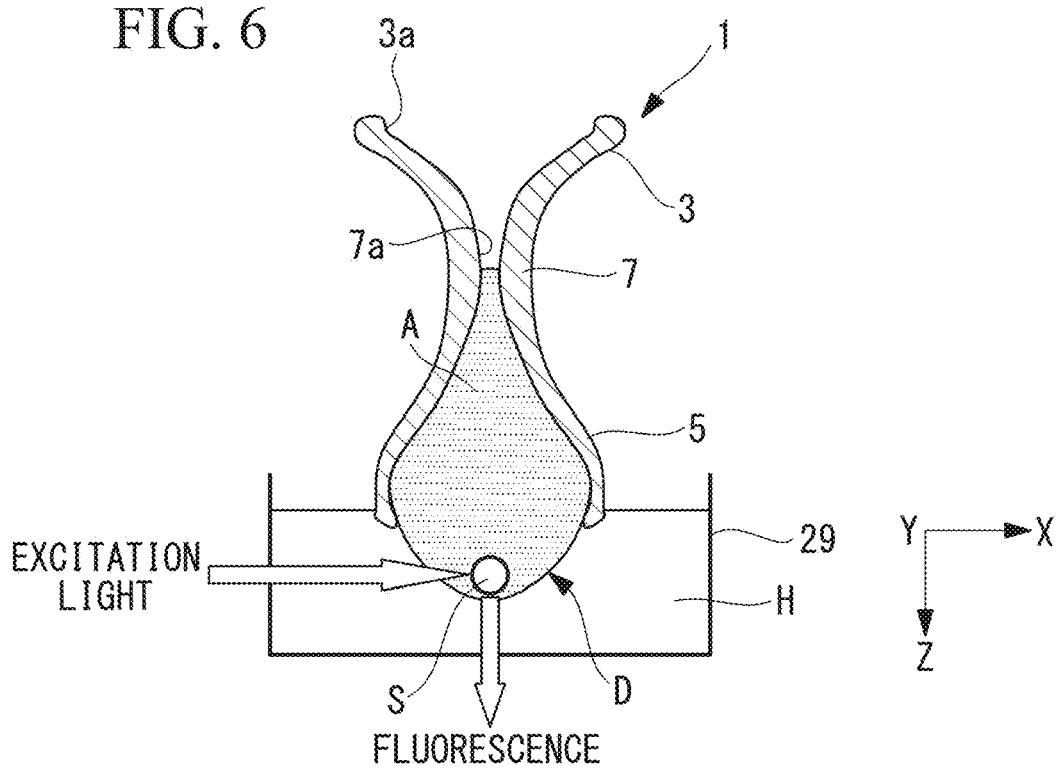
FIG. 6 is a longitudinal cross-sectional view showing a state in which fluorescence is generated by radiating excitation light onto an observation subject included in the gel-like hanging drop in FIG. 5.

Next, as shown in FIG. 6, a transparent container 29 in which a solution H having a refractive index that is equivalent to that of the medium solution A forming the hanging drop D is stored is prepared. Then, in a state in which the hanging drop D is immersed in the solution H, the observation subject S included in the hanging drop D is observed and screened by using a light-sheet microscope (not shown) (step S3).

In this case, excitation light flatly focused along a plane that is orthogonal to the vertical direction (Z-direction) may be made laterally incident on the hanging drop D, thus irradiating the observation subject S. Then, out of the fluorescence generated in the observation subject S, the fluorescence radiated downward in the vertical direction from the bottom portion of the hanging drop D may be collected by an objective lens (not shown). In this case, by aligning the focal position of the excitation light in the observation subject S and a detection optical axis and by also aligning a focal surface of the objective lens with the incident plane of the excitation light, the fluorescence generated over a wide area along the focal surface of the objective lens is collected all at once by the objective lens, and thus, it is possible to easily acquire a clear fluorescence image of the observation site in the observation subject S.

Figure 7:
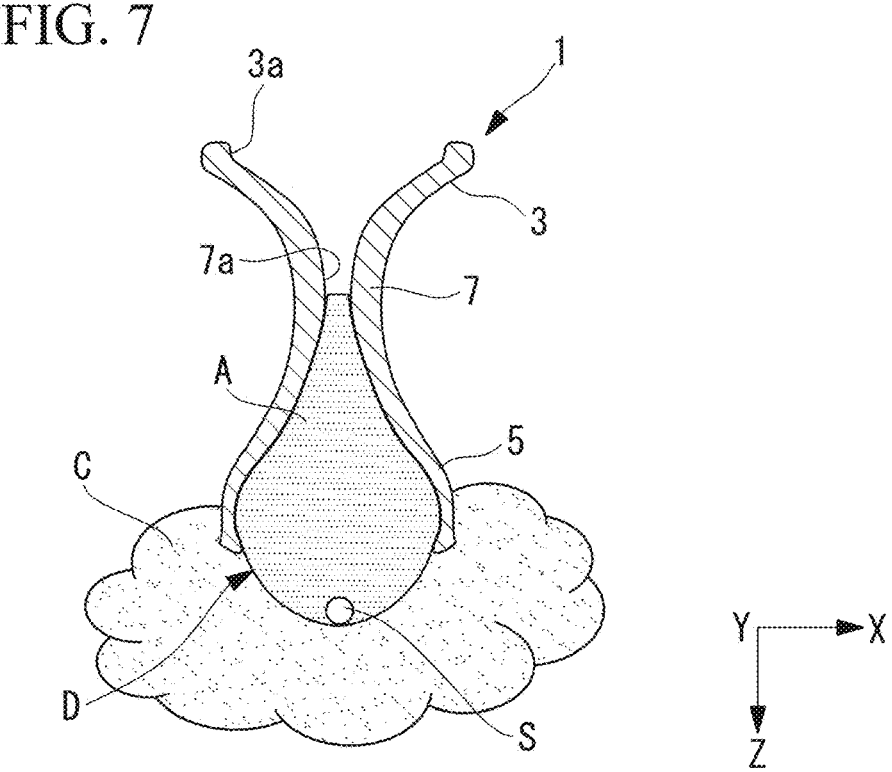
FIG. 7 is a longitudinal cross-sectional view showing a state in which the gel-like hanging drop in FIG. 6 is brought into contact with a liquid in a mist-like state that liquefies the drop.

Next, the gel-like hanging drop D is liquefied again by means of the sample processing method according to this embodiment (step S4). Specifically, first, as shown in FIG. 3, the liquid C is stored in the container 11, and the hanging-drop forming device 1 in which the gel-like hanging drop D is supported is supported by the support 9 and disposed the liquid C in the container 11. Then, the ultrasonic nebulizing apparatus 13 is activated to nebulize the liquid C, the container 11 is filled with the mist-like liquid C, and thus, as shown in FIG. 7, the liquid C is brought into contact with the surface of the gel-like hanging drop D in a mist-like manner.

Figure 8A:
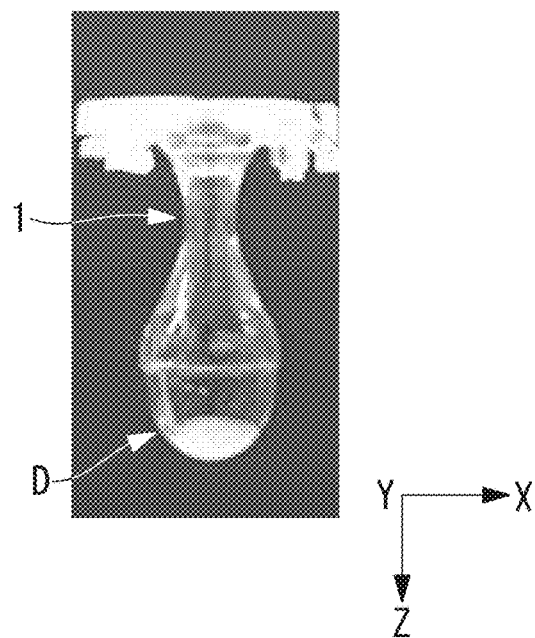
FIG. 8A is a diagram showing an example of an image acquired by performing bright-field observation of the liquefied hanging drop.
Figure 8B:
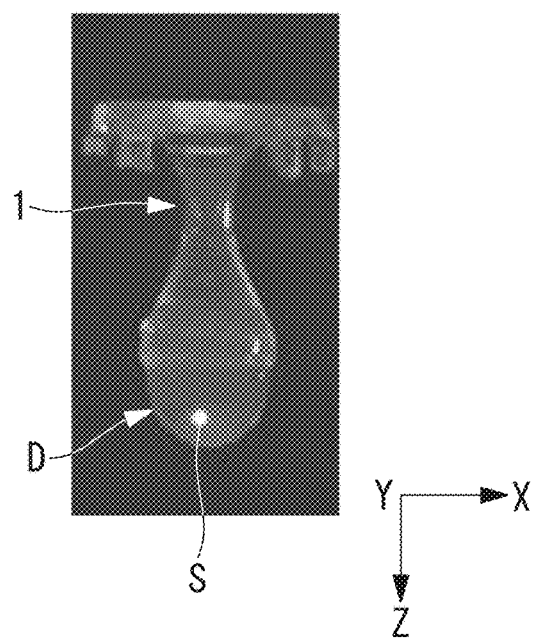
FIG. 8B is a diagram showing an example of an image acquired by performing fluorescence observation of the liquefied hanging drop

The hanging drop D in this state is left standing still in the mist-like liquid C for one hour, the liquid C permeates into the interior of the hanging drop D from the exposed surface thereof, and thus, the hanging drop D is liquefied up to the vicinity of the area surrounding the observation subject S. By doing so, for example, as shown in FIGS. 8A and 8B, the hanging drop D is liquefied while maintaining the state in which the hanging drop D is supported by the hanging-drop forming device 1 while the observation subject S is included therein.

By liquefying the hanging drop D, it becomes possible to perform medium exchange via the depression 3 from above the hanging-drop forming device 1. FIG. 8A shows an example of an image acquired by performing bright-field observation of the liquefied hanging drop D, and it is clear that the gel-like medium solution A remains in the area surrounding the observation subject S. FIG. 8B shows an example of an image acquired by performing fluorescence observation of the liquefied hanging drop D, and it is possible to visually confirm the observation subject S included in the hanging drop D.

Figure 9:
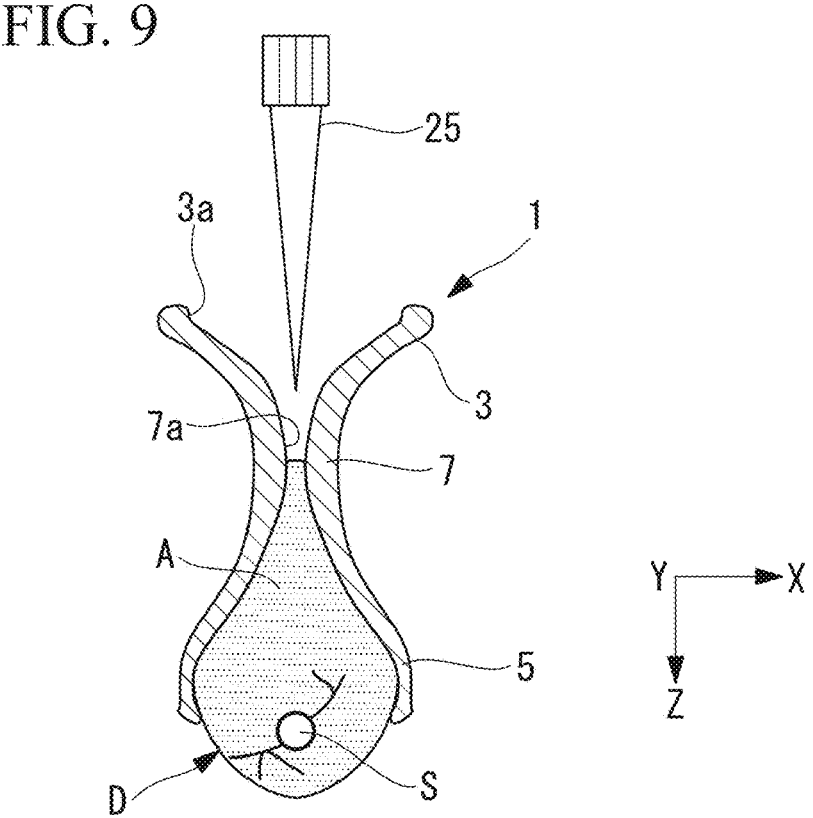
FIG. 9 is a longitudinal cross-sectional view showing a state in which the observation target in the hanging drop that has completed terminal culturing is recovered by using a pipette.

Next, as shown in FIG. 9, after completing terminal culturing, which is the final culturing, the observation subject S is continued to be cultured in the liquid hanging drop D or the observation subject S is recovered from the liquid hanging drop D to be transplanted to a mouse or the like.

As has been described above, with the sample processing method and the sample culturing method according to this embodiment, as a result of maintaining the state in which the medium solution A is supported by the hanging-drop forming device 1 while the observation subject S is included therein even after the medium solution A is liquefied, it is possible to perform work such as medium exchange and continuous culturing on the same hanging-drop forming device 1. In addition, it is possible to prevent the observation subject S from being exposed to the liquid C, which liquefies the medium solution A, as a result of the observation subject S becoming exposed, and it is also possible to prevent the observation subject S from adhering to a bottom surface of the container 11 accommodating the liquid C or changing the form thereof as a result of coming into contact with the bottom surface of the container 11. Furthermore, as compared with the case in which the hanging drop D is liquefied after being removed from the hanging-drop forming device 1, it is possible to reduce the number of work steps and the amount of materials. Therefore, with the sample formed by gelating the medium solution A in which the observation subject S is included, it is possible to easily perform recovery of the observation subject S, medium exchange, and continuous culturing.

In this embodiment, although the liquid C is brought into contact with the gel-like hanging drop D in a mist-like manner, it is not limited to this method so long as it is possible to maintain the state in which the medium solution A is supported by a substrate such as the hanging-drop forming device 1 or the like while the observation subject S is included therein by making the liquid C act on the gel-like medium solution A.

In addition, in this embodiment, although the hanging drop is liquefied up to the vicinity of the area surrounding the observation subject S, depending on the purpose, only the interior of the hanging drop D may be liquefied leaving the surface thereof in a gel-like state, or only the surface of the hanging drop D may be liquefied leaving the area surrounding the hanging drop D in a gel-like state.

For example, instead of the ultrasonic nebulizing apparatus 13, another apparatus that is capable of nebulizing the liquid C, such as a nebulizer or the like that nebulizes the liquid C by means of ultrasonic waves or pressurization, may be employed. In addition, instead of nebulizing the liquid C, the liquid C may be brought into contact with the surface of the droplet A' of the medium solution A, for example, by forming droplets having smaller volumes than that of the droplet A' of the medium solution A, such as in the form of a foam or a spray. In this case, for example, a spraying apparatus, a sputtering apparatus, a pump, or the like may be employed as a means for achieving contact with the liquid. This is also applicable to an apparatus that makes the liquid B act on the liquid medium solution A by means of nebulizing or the like.

Figure 10:
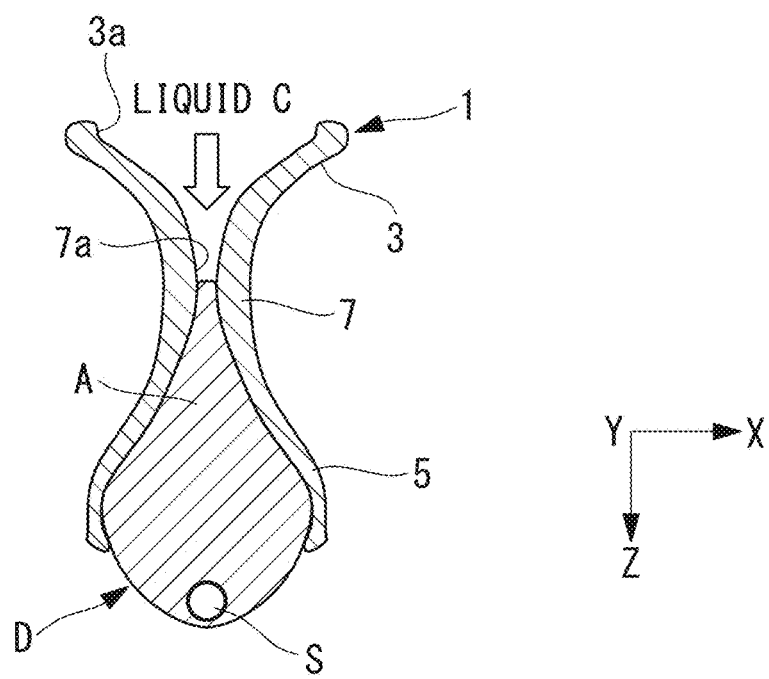
FIG. 10 is a longitudinal cross-sectional view showing a state in which the liquid that liquefies the gel-like hanging drop is added to the gel-like hanging drop in FIG. 4.

In addition, for example, as shown in FIG. 10, in the state in which the hanging drop is supported by the hanging-drop forming device 1, the liquid C may be added to the hanging drop D via the depression 3 by using a pipette or the like. In this case, it is possible to add a drug or a culturing liquid to the liquefied interior of the hanging drop D via the depression 3 from above the hanging-drop forming device 1 even if the surface of the hanging drop D of the medium solution A is left in a gel-like state.

Figure 11:
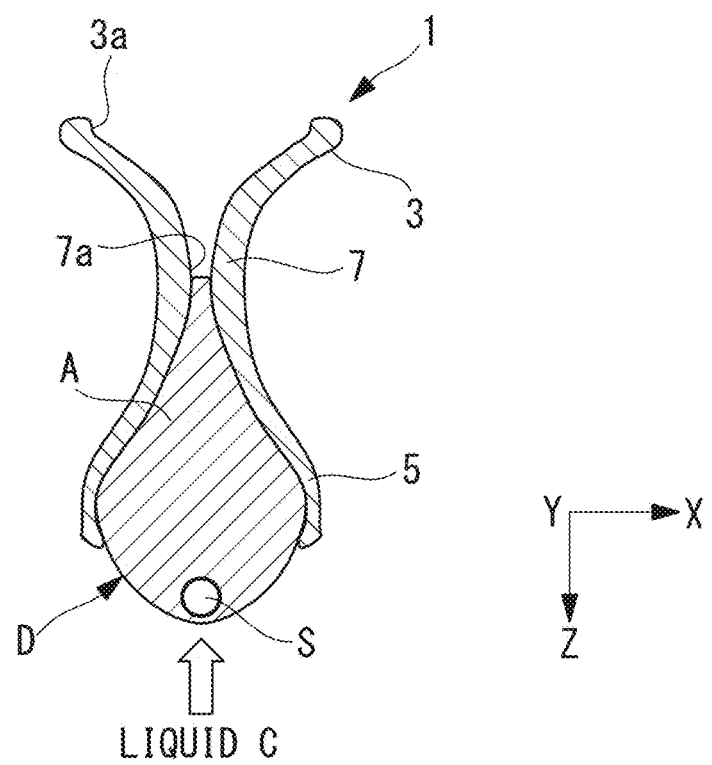
FIG. 11 is a longitudinal cross-sectional view showing a state in which the liquid that liquefies the gel-like hanging drop is applied to the gel-like hanging drop in FIG. 4.

In addition, for example, as shown in FIG. 11, in the state in which the hanging drop D is supported by the hanging-drop forming device 1, the liquid C may be applied, by using a sponge or the like, to the surface of the hanging drop D exposed from the hanging-drop-forming section 5.

Figure 12:
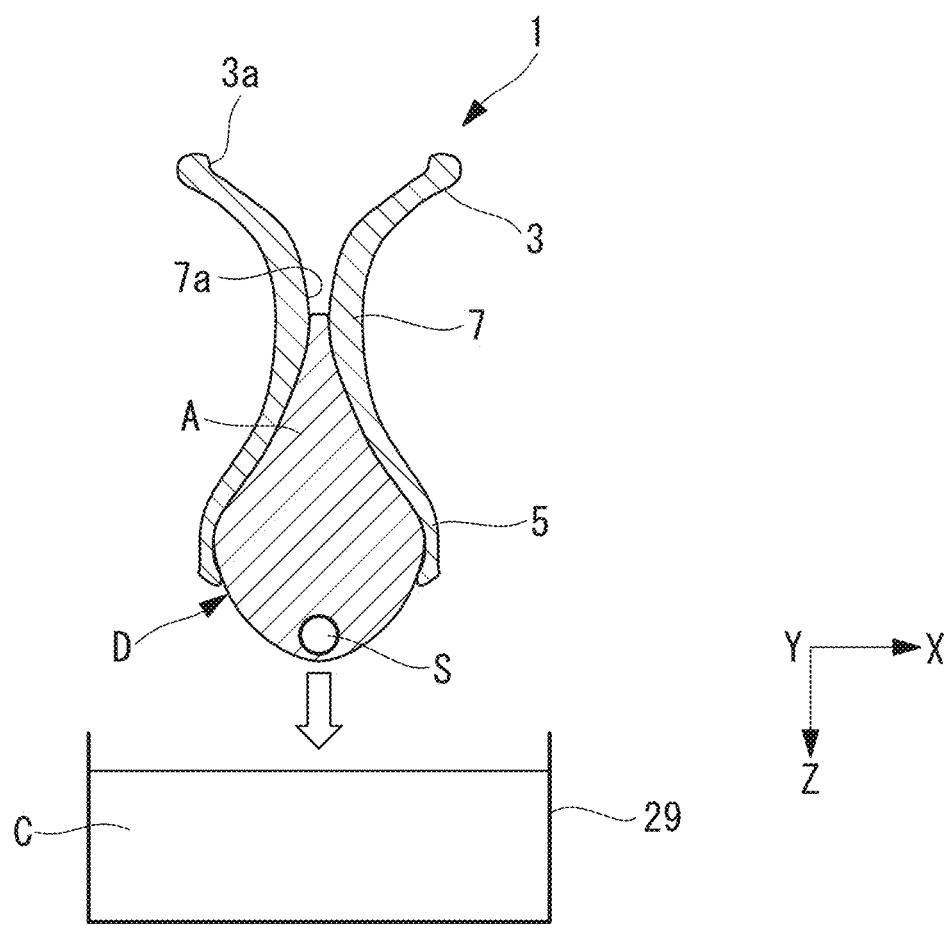
FIG. 12 is a longitudinal cross-sectional view showing a state in which the gel-like hanging drop in FIG. 4 is immersed in the liquid that liquefies the drop.

In addition, as shown in FIG. 12, the liquid C may be stored in the container 29, and the hanging drop D supported by the hanging-drop forming device 1 may be immersed in the liquid C. In this case, in order to prevent the liquefied hanging drop D from being mixed and dispersed in the liquid C, for example, after immersing the gel-like hanging drop D in the liquid C, the hanging drop D may be taken out from the liquid C before a surface thereof is liquefied, and the hanging drop D may be liquefied by allowing the liquid C attached on the surface of the hanging drop D to permeate into the interior thereof.

In addition, in this embodiment, although the liquid C formed of the chelating agent has been described as an example of the liquid that liquefies the medium solution A, there is no limitation thereto. For example, in the case in which the gel-like droplet forming the hanging drop D includes two or more molecules joined by means of a cross-linking agent, a liquid that liquefies the droplet by means of an oxidative decomposition reaction that decomposes the cross-links thereof may be employed. In addition, in the case in which viscoelasticity is imparted to the gel-like droplet forming the hanging drop D by peptides, fibers, sugars or lipids, a liquid that liquefies the droplet by means of a reaction that enzymatically or chemically decomposes the peptides, the fibers, the sugars or the lipids may be employed.

In addition, in this embodiment, although a spheroid has been described as an example of the observation subject, alternatively, a biological origin material formed of, for example, cells, cell aggregates, cellular tissue, organoids, or the like may be employed. Examples of cells include cells originating from vertebrate animals such as humans, mice, rats, dogs, monkeys, rabbits, goats, cows, horses, pigs, cats, and the like, cells originating from invertebrate animals such as fruit flies, silkworms, and the like, microorganisms such as yeast, $E.$ $coli$, and the like, pluripotent stem cells, such as ES cells, iPS cells, and the like, and stem cells such as mesenchymal stem cells, fat stem cells, hematopoietic stem cells, neural stem cells, hepatic stem cells, muscle stem cells, and the like. In addition, a non-biological origin material that generates fluorescence, light, or phosphorescence or that has a pigment may be employed as the observation subject.

In this embodiment, although the hanging-drop forming device 1 formed of one set of the depression 3, the hanging-drop-forming section 5 and the duct 7 has been described as an example of the substrate, a multiwell plate configured by arranging multiple sets of the depression 3, the hanging-drop-forming section 5 and the duct 7 in an array-like manner may be employed. By employing such a multiwell plate, it is easy to perform automatic dispensing, and it is possible to perform, with a high throughput, image acquisition for a large amount of spheroids for the purpose of screening. In addition, it is possible to identify a plurality of hanging drops D all at once, and it is possible to easily cope with robotization.

In addition, in this embodiment, although the case in which the hanging drop D is formed by means of the hanging-drop forming device 1 has been described as an example, as long as it is possible to make the liquid C act on the medium solution A in a state in which the medium solution A is supported by the substrate, the medium solution A need not be supported in a suspended state. In addition, it suffices that the substrate is capable of supporting the medium solution A with the surface of the medium solution A with which the liquid C is brought into contact exposed, and the substrate may have, for example, a rod-like, cup-like, well-like, ring-like, or swab-like form, a plate-like form having a flat or irregular surface, a sponge-like form, or a porous form. In particular, it is preferable that the surface of the substrate be processed so that the medium solution A easily attaches thereto to be supported thereon.

Figure 13A:
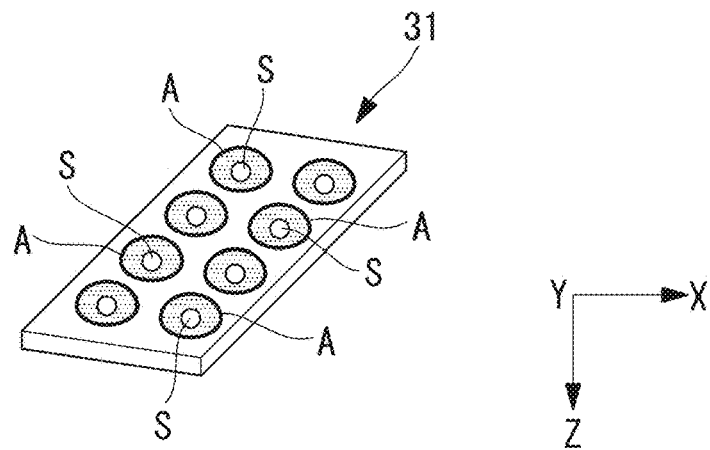
FIG. 13A is a perspective view showing an example of a medium solution that is adhered to a slide glass in a droplet-like manner and that is gelated in that state.
Figure 13B:
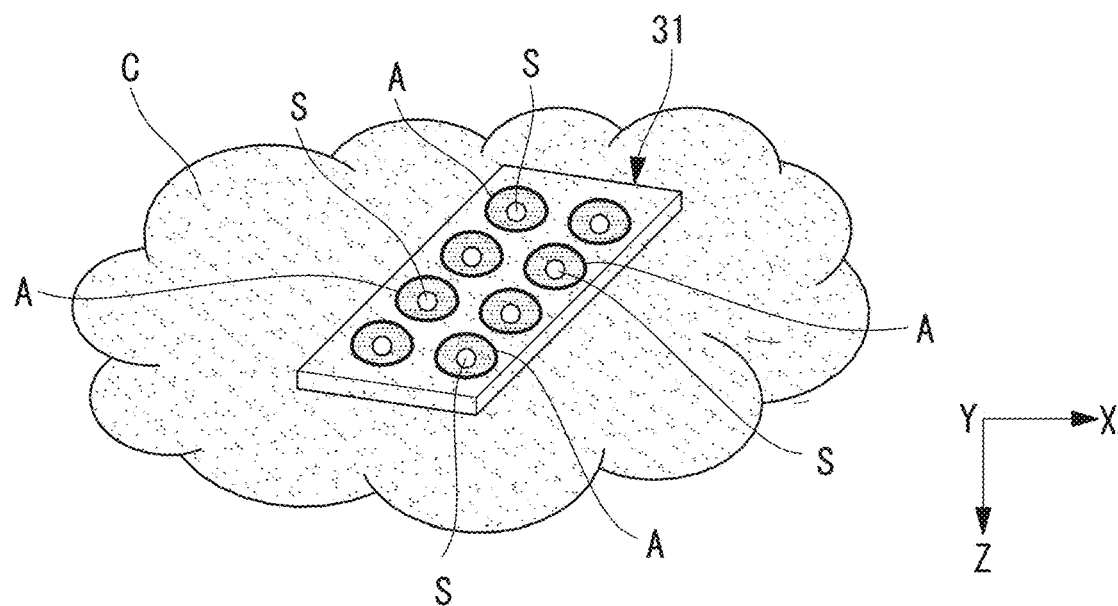
FIG. 13B is a perspective view showing a state in which the droplet of the medium solution in FIG. 13A is brought into contact with the liquid in a mist-like state that liquefies the droplet.
Figure 13C:
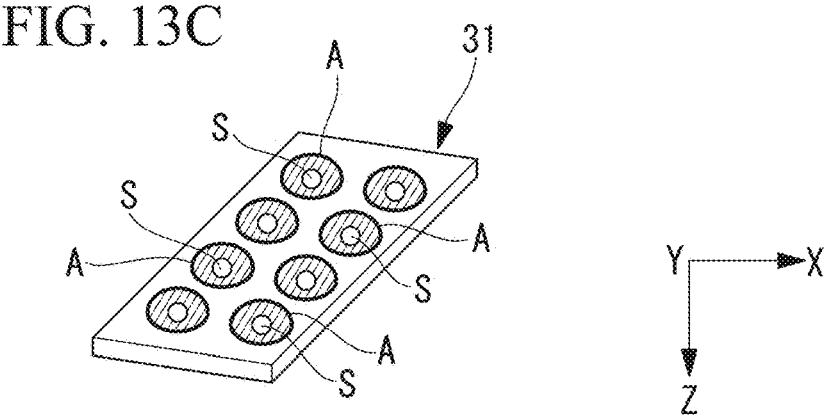
FIG. 13C is a perspective view showing a state in which an exposed surface of the droplet of the medium solution in FIG. 13B is liquefied.

For example, as shown in FIGS. 13A to 13C, a plate-like slide glass (desirably, with a hydrophobic coating) 31 having a flat or irregular surface maybe employed as the substrate. In this case, as shown in FIG. 13A, the sample may be formed by dripping and attaching the medium solution A on one surface of the slide glass 31 in a droplet-like manner, and by gelating an exposed surface of the droplet in which the observation subject S is included.

In this case, as shown in FIG. 13B, the mist-like liquid C may be sprayed on the droplet of the gel-like medium solution A on the slide glass 31, the liquid C may be brought into contact with the exposed surface of the droplet of the medium solution A in a mist-like manner, and the droplet of the medium solution A may be liquefied, as shown in FIG. 13C.

In addition, by flipping over the droplet of the medium solution A gelated on the slide glass 31 shown in FIG. 13A together with the slide glass 31, the sample supported on the bottom surface of the slide glass 31 may also be liquefied by bringing the liquid C into contact with the droplet of the gel-like medium solution A thereof in a mist-like manner.

Note that the substrate may be manufactured by using, for example, an inorganic substance including glass, and the like, or alternatively, organic substances including similar substances, derivatives, friends, and the like, such as synthetic rubber, dimethyl siloxane, silicone resin, natural rubber, fluorinated polymer, polyurethane, polyethylene, polyethylene terephthalate, polyvinyl chloride, polyolefin, polycarbonate, polystyrene, polydimethylsiloxane, polysiloxane-based polymer, polymethyl acrylatem, polymethyl hydrogen siloxane, and polymethylmethacrylatemethyl hydrogen siloxane. The substrate may be manufactured by using one of or a plurality of these raw materials.

As has been described above, although the embodiment of the present invention has been described in detail with reference to the drawings, the specific configuration is not limited to that of this embodiment, and design alterations or the like within a range that does not deviate from the scope of the present invention are also encompassed. For example, the present invention is not limited to the forms employed in the above-described embodiment and modifications, and the present invention may be employed in an embodiment in which the above-described embodiment and modifications are combined, as appropriate, and it is not particularly limited.

In addition, for example, although the gel-like medium solution A has been described as an example, the medium solution that is supported by the hanging-drop forming device 1 while the observation subject S is included therein may be in a solid state. In this case, it is permissible to employ, as the liquid C, a liquid that can maintain the state in which the solid-state medium solution is supported by the hanging-drop forming device 1 while the observation subject S is included therein by being added to the solid-state medium solution, by being brought into contact with the medium solution by being sprayed or applied on a surface thereof, or by immersing the solid medium solution therein.

As a result, the following aspects are derived from the above-described embodiment.

A first aspect of the present invention is a sample processing method including liquefying a medium solution by making a liquid that liquefies the medium solution act on a sample formed by gelating or solidifying the medium solution that is supported by a substrate while an observation subject is included therein, while maintaining the state in which the medium solution is supported by the substrate while the observation subject is included therein.

With this aspect, the state in which the medium solution is supported by the substrate while the observation subject is included therein is maintained even after the medium solution is liquefied. By doing so, it is possible to perform work such as medium exchange, continuous culturing, and the like on the same substrate. In addition, it is possible to prevent the observation subject from being exposed to the liquid, which liquefies the medium solution, as a result of the observation subject becoming exposed, and it is also possible to prevent the observation subject from adhering to a bottom surface of the container accommodating the liquid or changing the form thereof as a result of coming into contact with the bottom surface of the container. Therefore, with the sample formed by gelating or solidifying the medium solution in which the observation subject is included, it is possible to perform recovery of the observation subject, medium exchange, and continuous culturing.

In the above-described aspect, the liquid may be brought into contact with a surface of the medium solution in the form of a mist, a foam, or a droplet having a smaller volume than the medium solution.

By employing such a configuration, it is possible to prevent the medium solution from being mixed and dispersed in the liquid. In addition, since only simple work of bringing the liquid into contact with the surface of the medium solution in which the observation subject is included is required, it is possible to automate the processing for liquefying the medium solution of the sample.

In the above-described aspect, the liquid may be nebulized by means of ultrasonic-wave irradiation or pressurization.

By employing such a configuration, it is possible to make the liquid into a mist in a simple manner by means of a general method.

In the above-described aspect, the liquid may be added or applied to the medium solution or the medium solution is immersed in the liquid.

By employing such a configuration, in the case in which the liquid is added to the medium solution, it is possible to add a drug or a culturing liquid by liquefying the interior of the sample while leaving the surface of the sample in a gel-like or solid state. In addition, in the case in which the medium solution is immersed in the liquid, it suffices to just store the liquid in a container, and thus, it is possible to simplify the apparatus.

In the above-described aspect, the liquid may liquefy the medium solution by means of an oxidative decomposition reaction that decomposes cross-links in the sample in which two or more molecules are joined by cross-linking agents, a chelating reaction that eliminates joining of molecules by removing divalent cations from the sample in which two or more molecules are joined by divalent cations, or a reaction that enzymatically or chemically decomposes peptides, fibers, sugars, or lipids that impart viscoelasticity.

In the above-described aspect the liquid may be a chelating agent.

By employing such a configuration, it is possible to easily dissolve the gel-like or solid medium solution by means of the chelating agent.

In this case, the chelating agent may be formed of at least one of EDTA (ethylenediaminetetraacetic acid), EGTA (glycol ether diamine tetraacetic acid), and BAPTA 1,2-Bis(2-aminophenoxy)ethane-N,N,N',N'-tetraacetic acid).

In the above-described aspect, the liquid may contain an enzyme that exhibits alginate lyase activity.

In the above-described aspect, the substrate may have a rod-like, cup-like, well-like, ring-like, or swab-like form, a plate-like form having a flat or irregular surface, a sponge-like form, or a porous form.

In the above-described aspect, the substrate may support the medium solution including the observation subject therein in a state in which the medium solution is attached on a surface of the substrate in a droplet-like manner.

By employing such a configuration, by employing the substrate having a simple shape, it is possible to maintain the medium solution by utilizing surface tension.

In the above-described aspect, the substrate may support, in a suspended state, a droplet of the medium solution including the observation subject therein.

By employing such a configuration, it is possible to stabilize, by means of gravity, the position of the observation subject in the droplet of the medium solution while maintaining a state in which the droplet is separated from a well or the like.

In the above-described aspect, the sample may possess viscoelasticity due to alginic-acid hydrogel.

In the above-described aspect, the observation subject may be a biological origin material formed of cells, cell aggregates, cellular tissue, spheroids or organoids, or the observation subject may be a non-biological origin material that generates fluorescence, light, or phosphorescence or that has a pigment.

A second aspect of the present invention is a sample culturing method including: a step of gelating or solidifying a medium solution, which is substantially transparent when gelated or solidified, in a state in which the medium solution is supported by a substrate and includes an observation subject therein; a step of observing the observation subject that is included in the gel-like or solid medium solution supported by the substrate; and a step of, after performing observation, liquefying the medium solution by making a liquid that liquefies the medium solution act on the medium solution while maintaining the state in which the medium solution is supported by the substrate while the observation subject is included therein.

With this aspect, by gelating or solidifying the medium solution in the state in which the medium solution is supported by the substrate and the observation subject is included therein, it is possible to grow the observation subject or to change the medium in the gel-like medium solution supported by the substrate. Also, by observing the observation subject in this state, it is possible to perform highly detailed observation in which influence of the refractive index of the medium solution or the like is suppressed as compared with the case in which the medium solution is in a liquid state.

Furthermore, by liquefying the medium solution while maintaining the state in which the medium solution is supported by the substrate while the observation subject is included therein after performing observation, it is possible to perform work such as medium exchange, continuous culturing, and the like on the same substrate. In addition, it is possible to prevent the observation subject from being exposed to the liquid, which liquefies the medium solution, as a result of the observation subject becoming exposed, and it is also possible to prevent the observation subject from adhering to the bottom surface of the container accommodating the liquid or changing the form thereof as a result of coming into contact with the bottom surface of the container.

A sample processing method and a sample culturing method according to the present invention afford an advantage in that, with a sample formed by gelating or solidifying a medium solution including cells, it is possible to easily perform cell recovery, medium exchange, and continuous culturing.

REFERENCE SIGNS LIST 1 hanging-drop forming device (substrate)
31 slide glass (substrate)
A medium solution
C liquid
S observation subject (biological origin material)

The invention claimed is:

1. A sample processing method comprising:
    liquefying at least part of a sample which is supported on a substrate as a hanging droplet and comprises a medium that contains alginate and is at least partially gelled or solidified, by causing a liquid comprising an alginate lyase or a chelating agent to act on the at least partially gelled or solidified medium,
    wherein the sample includes an observation subject therein, and
    wherein the substrate that supports the sample has a shape such that after the medium is at least partially liquefied, a resulting medium solution having a droplet shape remains supported as the hanging droplet by the substrate.

2. The sample processing method according to claim 1, wherein the liquid is brought into contact with a surface of the medium as a mist, a foam, or a droplet having a smaller volume than the medium.

3. The sample processing method according to claim 2, wherein the liquid is nebulized by ultrasonic-wave irradiation or pressurization.

4. The sample processing method according to claim 1, wherein the liquid is added or applied to the medium or the medium is immersed in the liquid.

5. The sample processing method according to claim 1, wherein the liquid at least partially liquefies the medium by an oxidative decomposition reaction that decomposes cross-links in the sample in which two or more molecules are joined by cross-linking agents, a chelating reaction that eliminates joining of molecules by removing divalent cations from the sample in which two or more molecules are joined by divalent cations, or a reaction that enzymatically or chemically decomposes peptides, fibers, sugars, or lipids that impart viscoelasticity.

6. The sample processing method according to claim 5, wherein the liquid comprises a chelating agent.

7. The sample processing method according to claim 6, wherein the chelating agent comprises at least one of EDTA (ethylenediaminetetraacetic acid), EGTA (glycol ether diamine tetraacetic acid), and BAPTA (1,2-Bis(2-aminophenoxy)ethane-N,N,N',N'-tetraacetic acid).

8. The sample processing method according to claim 5, wherein the liquid contains an alginate lyase.

9. The sample processing method according to claim 6, wherein the sample comprises an alginic-acid hydrogel and possesses viscoelasticity.

10. The sample processing method according to claim 1, wherein the observation subject is a biological origin material formed of cells, cell aggregates, cellular tissue, spheroids or organoids.

11. The sample processing method according to claim 1, wherein the observation subject is a non-biological origin material that generates fluorescence, light, or phosphorescence or that has a pigment.

12. A sample culturing method comprising:
- at least partially gelating or solidifying a sample that is supported on a substrate as a hanging droplet and includes an observation subject therein, to obtain an at least partially gelled or solidified medium that contains alginate, is substantially transparent, is supported on the substrate as the hanging droplet, and includes the observation subject therein;
- observing the observation subject that is included in the medium; and
- after performing observation, at least partially liquefying the medium by causing a liquid comprising an alginate lyase or a chelating agent to act on the at least partially gelled or solidified medium,
- wherein the substrate that supports the sample has a shape such that after the medium is at least partially liquefied, a resulting medium solution having a droplet shape remains supported as the hanging droplet by the substrate.

* * * * *